(12) United States Patent
Sugimoto

(10) Patent No.: US 7,762,946 B2
(45) Date of Patent: Jul. 27, 2010

(54) ELECTRONIC ENDOSCOPE SYSTEM CAPABLE OF DISPLAYING A PLURALITY OF IMAGES

(75) Inventor: Hideo Sugimoto, Tokyo (JP)

(73) Assignee: Hoya Corporation, Tokyo (JP)

( * ) Notice: Subject to any disclaimer, the term of this patent is extended or adjusted under 35 U.S.C. 154(b) by 954 days.

(21) Appl. No.: 11/168,463

(22) Filed: Jun. 29, 2005

(65) Prior Publication Data

US 2005/0288553 A1 Dec. 29, 2005

(30) Foreign Application Priority Data

Jun. 29, 2004 (JP) ............................. 2004-191932

(51) Int. Cl.
*A61B 1/04* (2006.01)
(52) U.S. Cl. .......................... 600/109; 600/118; 348/65
(58) Field of Classification Search ................. 600/101, 600/109, 118, 160, 178, 180, 181, 407, 476–478; 348/65, 68, 74; 382/128, 277, 293, 294, 382/298
See application file for complete search history.

(56) References Cited

U.S. PATENT DOCUMENTS

| 5,749,830 | A | * | 5/1998 | Kaneko et al. ............... 600/160 |
| 5,803,914 | A | * | 9/1998 | Ryals et al. .................. 600/407 |
| 5,871,439 | A | * | 2/1999 | Takahashi et al. ............ 600/118 |
| 6,099,466 | A | * | 8/2000 | Sano et al. ................... 600/160 |
| 6,611,846 | B1 | | 8/2003 | Stoodley .................. 707/104.1 |
| 6,635,011 | B1 | * | 10/2003 | Ozawa et al. ................ 600/178 |
| 7,324,674 | B2 | * | 1/2008 | Ozawa et al. ................ 382/128 |
| 7,453,490 | B2 | * | 11/2008 | Gunday ........................ 348/68 |
| 7,457,656 | B2 | * | 11/2008 | Judd et al. .................... 600/407 |
| 7,466,871 | B2 | * | 12/2008 | Hosoda et al. ............... 382/266 |
| 7,574,250 | B2 | * | 8/2009 | Niemeyer .................... 600/427 |
| 7,581,191 | B2 | * | 8/2009 | Rice et al. .................... 715/764 |
| 2002/0026099 | A1 | * | 2/2002 | Adachi et al. ................ 600/178 |
| 2003/0142205 | A1 | * | 7/2003 | Takahashi et al. ............. 348/65 |

(Continued)

FOREIGN PATENT DOCUMENTS

JP 2-131740 5/1990

(Continued)

OTHER PUBLICATIONS

English Language abstract of JP9-66023.

(Continued)

*Primary Examiner*—John P Leubecker
*Assistant Examiner*—Samuel Candler
(74) *Attorney, Agent, or Firm*—Greenblum & Bernstein P.L.C.

(57) ABSTRACT

An electronic endoscope system, which is adapted to observe a fluorescence image of autofluorescence emitted from a body cavity wall irradiated with excitation light as well as a normal image of the body cavity wall illuminated with white light on a display device, includes a display controller whereby the aspect ratio of at least one of a plurality of images to display is converted so that the plurality of images are displayed in conformity with the shape of a display area of the display device when the plurality of images including the normal image and the fluorescence image are displayed on the display device. In the electronic endoscope system, the display controller converts the aspect ratio of at least one of the plurality of images by cutting both horizontal ends of the image to convert.

18 Claims, 7 Drawing Sheets

U.S. PATENT DOCUMENTS

2004/0186351 A1* 9/2004 Imaizumi et al. ............ 600/160
2005/0073578 A1* 4/2005 Odlivak et al. ................ 348/65
2005/0154289 A1* 7/2005 Judd et al. .................. 600/407

FOREIGN PATENT DOCUMENTS

| JP | 9-66023 | 3/1997 |
|---|---|---|
| JP | 2001-137183 | 5/2001 |
| JP | 2002-291692 | 10/2002 |
| JP | 2002-291694 | 10/2002 |
| JP | 2003-33324 | 2/2003 |

OTHER PUBLICATIONS

U.S. Appl. No. 11/186,905, filed Jul. 22, 2005.
U.S. Appl. No. 11/168,304, filed Jun. 29, 2005.

* cited by examiner

ELECTRONIC ENDOSCOPE SYSTEM CAPABLE OF DISPLAYING A PLURALITY OF IMAGES

BACKGROUND OF THE INVENTION

The present invention relates to an electronic endoscope system that is adapted to observe a fluorescence image of autofluorescence emitted from a body cavity wall irradiated with excitation light, as well as a normal image of the body cavity wall illuminated with white light, on a display device such as a monitor.

An example of such an electronic endoscope system is disclosed in Japanese Patent Provisional Publications No. HEI 9-066023. The system disclosed in this publication includes a first solid-state imaging device that takes a fluorescence image, and a second solid-state imaging device that takes an RGB color image in accordance with a frame sequential-method. In the system, signals outputted film the first and second solid-state imaging devices are processed by video circuits for fluorescence images and for normal images, respectively. The signals are then synthesized by an image synthetic circuit, and are displayed on a monitor device. According to the operation of a display image selector switch, one of the two kinds of images or both is displayed on the monitor device.

Another example is disclosed in Japanese Patent Provisional Publication No. P2003-33324A. FIG. 12 shows a block diagram of the system that is illustrated in FIG. 16 of this publication. The system disclosed in this publication includes (see FIG. 12) a first lamp 124 that emits illuminating light for normal observation and a second lamp 125 that emits excitation light, and either one of the two kinds of light is selectively introduced into a light guide 133 by changing the position of a movable mirror 128. Image signals captured by CCD 137 are stored in a first memory 141 and a second memory 142, and are then displayed on a Hi-Vision monitor 115 through a display location selector circuit 144. When a selector switch for displaying two images (hereinafter, referred to as a two-image-display switch) is turned ON, a normal image and a fluorescence image are displayed on the Hi-Vision monitor 115, simultaneously.

Since the image data captured by the imaging device has an aspect ratio (for example, 4:3) equivalent to the aspect ratio of the monitor's display area, the display area is effectively used when either one of the normal image and the fluorescence image is separately displayed without any special processing being applied. However, when both kinds of images are displayed side by side as described above, the display area is not effectively used, and each image becomes small. Consequently, it is difficult to make a diagnosis with checking the details of the image. The latter publication discloses a technology of maintaining each image size by using the Hi-Vision monitor that has a larger aspect ratio of the horizontal length of the display area to the vertical length thereof. However, if such a relatively expensive Hi-Vision monitor is used, the entire system cost will arise.

SUMMARY OF THE INVENTION

The present invention is advantageous in that an electronic endoscope system is provided that is capable of preventing each image from being small so as to facilitate a diagnosis using a monitor which has the same aspect ratio as an image data captured by an imaging device when a normal image and a fluorescence image are displayed simultaneously.

According to an aspect of the invention, there is provided an electronic endoscope system used for observing living tissues inside a body cavity, provided with an image capturing system capable of capturing images of the living tissues, a display device having an image displaying area, each of the images captured by the image capturing system and the image displaying area having similar rectangular shapes defined by a predetermined aspect ratio, a display control system that controls the display device to display a plurality of images in the image displaying area of the display device along a direction parallel with one side of the rectangular shape, and a data conversion system that converts at least one of the plurality of images to be displayed in the image displaying area such that at least a side end portion of the image in the direction in which the plurality of images are aligned is eliminated, the remaining portion of the converted image being displayed such that a length of the converted image in the direction in which the plurality of images are aligned is unchanged on the image displaying area.

Optionally, the display controller may allow the display device to display the normal image and the fluorescence image side by side in the longitudinal direction (long side direction) of a screen of the display device, converting the aspect ratio of at least one of the two images by cutting at least one of both longitudinal ends of the image to convert.

Further optionally, the display controller may convert the aspect ratio of at least one of the two images by cutting both longitudinal ends of the image to convert.

Still optionally, the electronic endoscope system may further include at least one conversion-assignment switch that specifies an image of which the aspect ratio should be converted. In the system, the display controller may convert the aspect ratio of an image that is specified by the conversion-assignment switch, and allows the display device to display the converted image.

Furthermore, the electronic endoscope may include a ROM that stores an identification data for identifying what kind of electronic endoscope is connected to the light source apparatus when the electronic endoscope is attached to the light source apparatus.

Optionally, the light source apparatus may include a rotary shutter inserted between the white light source and the light guide, the rotary shutter having a light transmitting area and a light blocking area, the white light being intermittently incident on the light guide as the rotary shutter rotates.

Further optionally, the light source apparatus may include an excitation light source driver that intermittently turns ON/OFF the excitation light source synchronously with the blocking/transmitting operation of the rotary shutter.

Optionally, the rotary shutter may be able to be shifted together with a beam combiner to a point that the rotary shutter does not interfere with the white light, the beam combiner combining both light paths of the white light and the excitation light.

Optionally, the image signal generating system may include a pre-signal-processing circuit that processes the image signals received from the imaging device, at least two image memories that store temporarily the image signals outputted from the pre-signal-processing circuit, and a post-signal-processing circuit that transforms the image signals outputted from the image memories into standardized video signals which are allowed to be displayed on the display device.

Still optionally, the display controller may include a system controller that controls the whole system, and a timing controller that takes timing control of the imaging device, the light source apparatus, the image signal generating system, and the display device based on commands from the system controller. The timing controller may give a command to the post-signal-processing circuit to control the timing for an image to be scaled up and down, to be given the aspect ratio conversion, and to be displayed.

Furthermore, the electronic endoscope may include an objective lens that is provided on the distal end surface of the insertion part, and an excitation light cut filter that is provided between the objective lens and the imaging device. The excitation light cut filter may eliminate the wavelength components equivalent to the excitation light from light directed to the imaging device from the objective lens.

Optionally, the excitation light source may emit near-ultraviolet light.

According to another aspect of the invention, there is provided an electronic endoscope system used for observing living tissues inside a body cavity, provided with an image capturing system capable of capturing images of the living tissues, a display device having an image displaying area, each of the images captured by the image capturing system and the image displaying area having similar rectangular shapes defined by a predetermined aspect ratio, a display control system that controls the display device to display a plurality of images in the image displaying area of the display device along a direction parallel with one side of the rectangular shape; and a data conversion system that converts at least one of the plurality of images to be displayed in the image displaying area such that at least a side end portion of the image in the direction in which the plurality of images are aligned is eliminated so that the aspect ratio of the at least one of the plurality of images displayed on the image displaying area is changed, the converted image being displayed such that a length of the converted image in the direction in which the plurality of images are aligned is unchanged on the image displaying area.

BRIEF DESCRIPTION OF THE ACCOMPANYING DRAWINGS

DETAILED DESCRIPTION OF THE EMBODIMENTS

Hereinafter, an electronic endoscope system according to an embodiment of the present invention will be described with reference to the accompanying drawings. The electronic endoscope system of the embodiment is directed to a system that is adapted to observe a fluorescence image of autofluorescence emitted from a body cavity wall irradiated with excitation light on a display device such as a monitor, as well as a normal image of the body cavity wall illuminated with white light.

Figure 1:
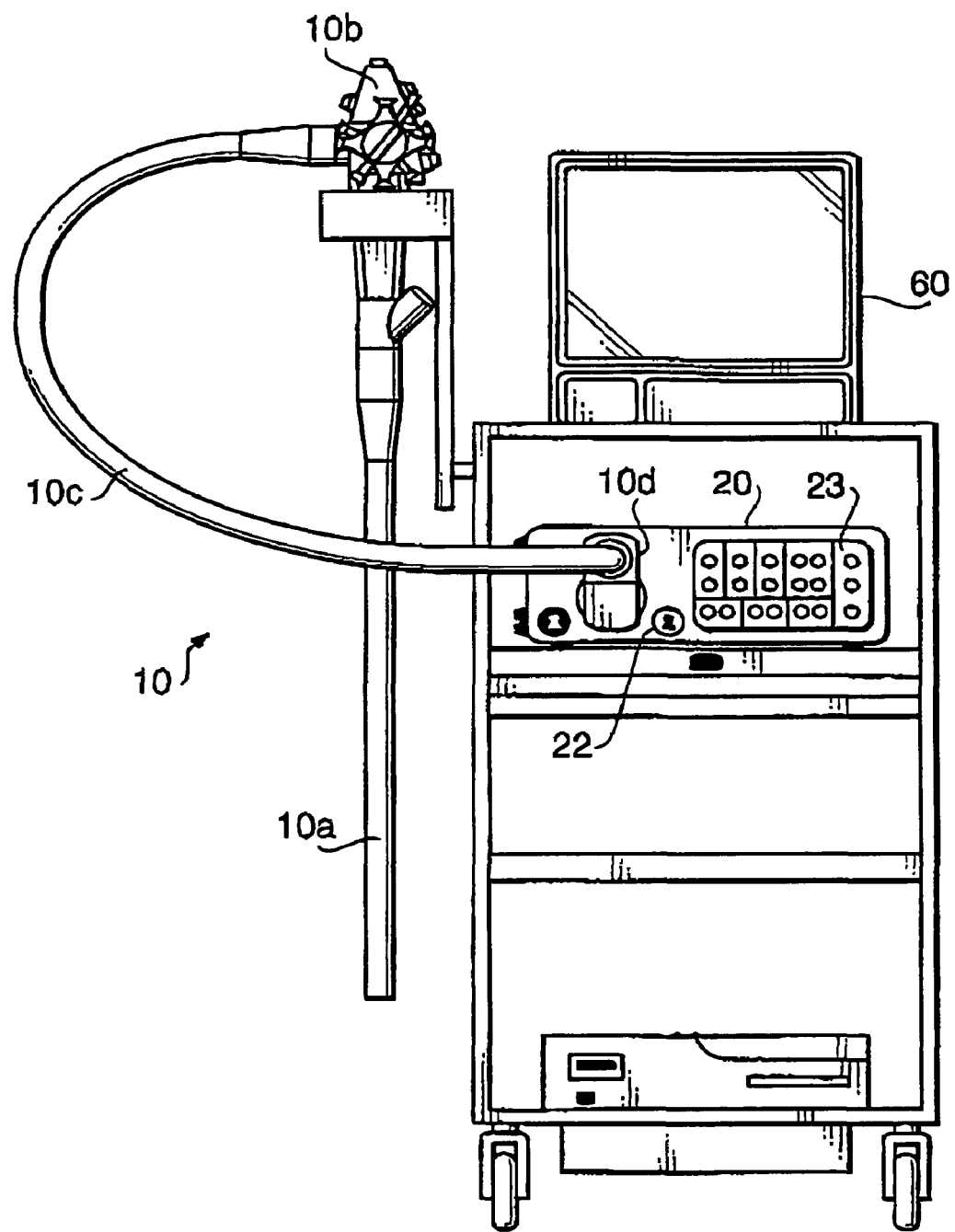
FIG. 1 is a front view of an electronic endoscope system according to an embodiment of the invention.
Figure 2:
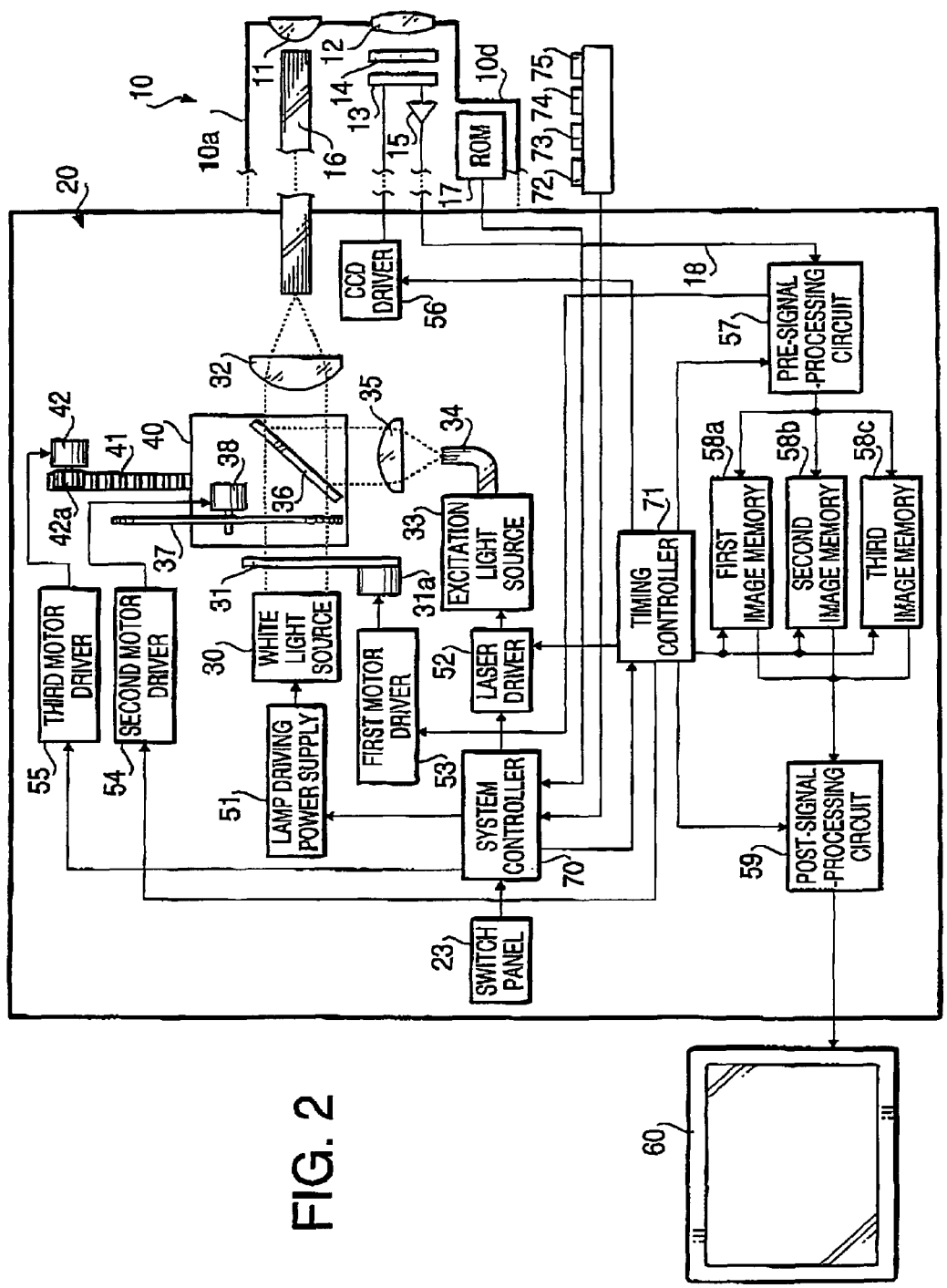
FIG. 2 is a block diagram illustrating an internal constitution of the electronic endoscope system shown in FIG. 1, especially showing a layout in the case of fluorescence observation.

FIG. 1 schematically shows an external view of an electronic endoscope system 1 according to an embodiment of the invention, and FIG. 2 shows a block diagram illustrating an internal constitution of the electronic endoscope system 1. As shown in FIG. 1, the electronic endoscope system is provided with a fluorescence observation endoscope 10, a light source apparatus 20, and a monitor 60. The display area of the monitor 60 applied to this embodiment has an aspect ratio of 4:3.

The fluorescence observation endoscope 10, which is adapted to fluorescence observation by modifying a usual electronic endoscope, is provided with an insertion part 10a that is formed long and slender so as to be inserted into the body cavity and has a flexible bendable part at the tip thereof, an operating part 10b that includes an angle knob and the like to operate the bendable part of the insertion part 10a, a flexible light guide tube 10c that connects the operating portion 10b with a light source apparatus 20, and a connector 10d that is provided at the rear anchor of the flexible light guide tube 10c.

The light source apparatus 20 supplies illuminating light and excitation light to the fluorescence observation endoscope 10, and, as described in detail below, has a function as an image signal generator that generates image signals from signals taken by the fluorescence observation endoscope 10 and a function as a display controller that converts the aspect ratio of at least one of the fluorescence image and the normal image and allows both the two images to be displayed when the fluorescence image and the normal images which have been taken are displayed simultaneously. On the front surface of the light source apparatus 20, there are provided with a key switch 22 for ON/OFF operation of a main power supply thereof, and a switch panel 23 on which various kinds of operation switches are arranged.

Hereinafter, according to FIG. 2, the constitutions of the fluorescence observation endoscope 10 and the light source apparatus 20 are explained in sequence. On the distal end surface of the insertion part 10a of the fluorescence observation endoscope 10, there are provided a light distribution lens 11 and an objective lens 12. Inside the tip portion of the insertion part 10a, there are incorporated an imaging device such as a CCD color imaging sensor that takes an object's color image formed by the objective lens 12, an excitation light cut filter 14 that eliminates the wavelength components equivalent to the excitation light for fluorescence excitation from the wavelength components of light directed to the imaging device 13 from the objective lens 12, and a cable driver 15 that amplifies image signals outputted from the imaging device 13.

Figure 3:
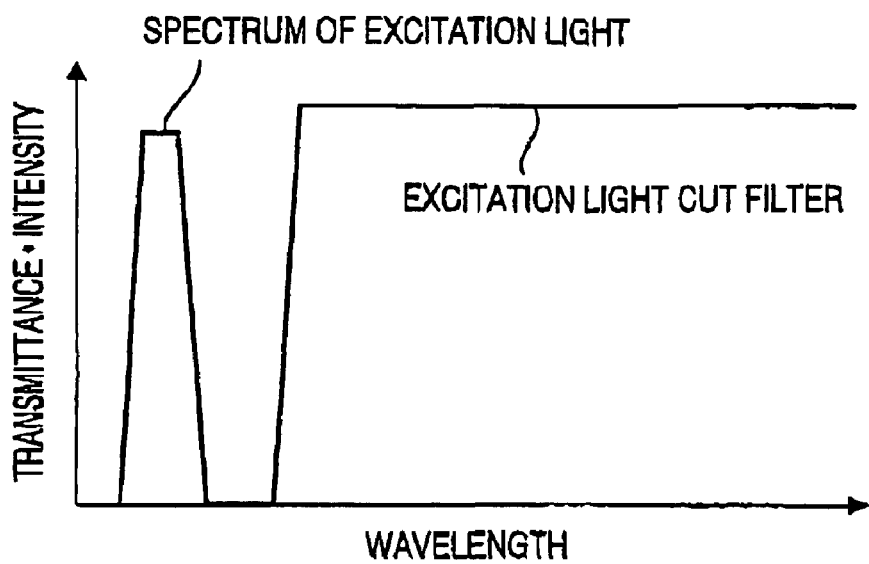
FIG. 3 is a graph illustrating transmission characteristics of an excitation light cut filter provided in an optical system in FIG. 2.

As shown in FIG. 3, the excitation light cut filter 14 has characteristics that cut off the excitation light and transmit light with wavelengths longer than the excitation light. Therefore, it is possible to prevent the excitation light, which is reflected by the wall of the body cavity subject to the observation, from being introduced into the imaging device 13 and to take only the fluorescence images during fluorescence observation. In addition, since near-ultraviolet light that excites autofluorescence of a living organism is applied as excitation light, even if the wavelength components of the excitation light is cut off by the excitation light cut filter 14, there is no trouble in taking a blue component, which is also generally used as excitation light, while taking normal color images.

A signal cable 18 that transmits the image signals amplified by the cable driver 15 runs through the insertion part 10a, the operation part 10b, and the flexible light guide tube 10c, and is connected to a signal processing circuit of the light source apparatus 20 that is connected to the fluorescence observation endoscope 10.

In parallel with the signal cable 18, a light guide 16 that is constituted by bundling plurality of optical fibers runs through the insertion part 10a, the operation part 10b, and the flexible light guide tube 10c. The tip end face of the light guide 16 faces the light distribution lens 11 within the tip portion of the insertion part 10a, and the rear anchor of the light guide 16 is fixed in the state to be inserted into the light source apparatus 20. In addition, a connection part 10d of the fluorescence observation endoscope 10 has a built-in ROM 17 for reading identification data when attached to the light source apparatus 20.

The light source apparatus 20 selectively introduces either white light for observation of the body cavity wall or the excitation light that excites the living tissues of the body cavity wall so that the living tissues emits autofluorescence into the end face of the rear anchor of the light guide 16. The light source apparatus 20 further processes the image signals received from the cable driver 15 to generate video signals, and then outputs the video signals to the monitor 60.

An optical system of the light source apparatus 20 is provided with a white light source (discharge tube lamp) 30 that emits substantially parallel white light (white light), a light control aperture 31 that controls the beam diameter of the white light emitted from the white light source 30, a condenser lens 32 that converges the white light which transmits the light control aperture 31 on the end face of the rear anchor of the light guide 16, an excitation light source 33 that emits the excitation light, an optical waveguide (single mode fiber) 34 that guides the excitation light emitted from the excitation light source 33, a collimating lens 35 that collimates the excitation light, which is diverging light emitted from the optical waveguide 34, and a dichroic mirror 36 that combines both light paths of the white light and the excitation light.

The light control aperture 31 is driven by an aperture driving motor 31a, and functions to control the intensity of the white light according to the reflectance of an object. The white light path that extends straight from the white light source 30 to the light guide 16 and the excitation light path that intersects perpendicularly therewith are combined by the light path combining device, that is, the dichroic mirror 36. Since the dichroic mirror 36 transmits the white light and reflects the near-ultraviolet light with wavelengths shorter than the white light, the dichroic mirror 36 transmits major part of the white light and reflects the excitation light, introducing both kinds of light into a single light path that extends to the end face of the rear anchor of the light guide 16.

Figure 4:
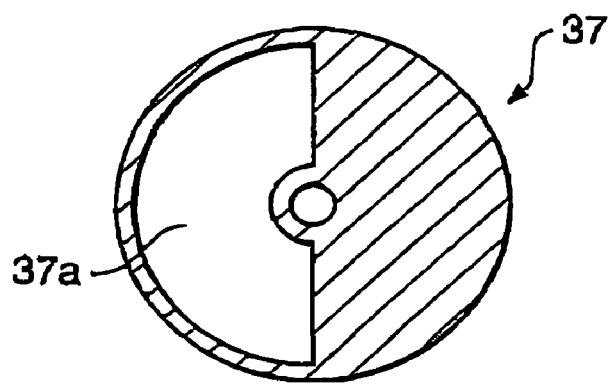
FIG. 4 is a front view of a rotary shutter provided in the optical system in FIG. 2.

Between the white light source 30 and the dichroic mirror 36A, there is arranged a rotary shutter 37 that enables the intermittent ON/OFF operation of the white light (that is, intermittently transmits or blocks the white light). The rotary shutter 37, as a front view thereof is shown in FIG. 4, has a fan-shaped window 37a with a center angle of 180 degrees, and the size of the window 37a is configured to be larger than the diameter of the beam of the white light. The rotary shutter 37 is allowed to rotate and intermittently transmit the white light as a shutter driving motor 38 is driven.

In addition, the dichroic mirror 36, the rotary shutter 37, and the shutter driving motor 38 are arranged in a unit 40 that is movable in the up-and-down direction in FIG. 2, that is, in the direction perpendicular to the white light path. A rack gear 41 extending along the moving direction thereof is fixed to the unit 40, and is geared with a pinion 42a of a unit driving motor 42. Rotating the unit driving motor 42 allows the unit 40 to move monolithically in the up-and-down direction so that the dichroic mirror 36 and the rotary shutter 37 can be shifted between both positions on and out of the white light path.

The light source apparatus 20 is provided with a lamp driving power supply 51 that supplies current to the white light source 30, a laser driver 52 that drives and switches the excitation light source 33, a first motor driver 53 that drives the aperture driving motor 31a, a second motor driver 54 that drives the shutter driving motor 38, a third motor driver 55 that drives the unit driving motor 42, and a CCD driver 56 that drives the imaging device 13. The light source apparatus 20 further includes a pre-signal-processing circuit 57 that processes image signals received from the cable driver 15, a first-third image memories 58a, 58b, and 58c that temporarily store digital image signals outputted from the pre-signal-processing circuit 57, a post-signal-processing circuit 59 that transforms the digital image signals outputted from the image memories into standardized video signals which are allowed to be displayed on a television monitor and outputs the standardized video signals, and a system controller 70 and a timing controller 71 that control all of the above components.

The system controller 70 is connected with a still image switch 72, a fluorescence mode switch 73, and first and second conversion-assignment switches 74 and 75 that are provided at the operation part 10b, and is farther connected electrically with various switches that are arranged on the switch panel 23. Based on the setting of each switches, the system controller 70 controls the lamp driving power supply 51 and the laser driver 52 so that the white light and the excitation light are emitted consecutively or stopped, and further controls the third motor driver 55 that drives the unit driving motor 42 to change the location of the unit 40 and to switch the display on the monitor 60. In addition, when the fluorescence observation endoscope 10 is connected to the light source apparatus 20, the built-in ROM 17 inside the fluorescence observation endoscope 17 is also connected to the system controller 70, which identifies that what is connected to the light source apparatus 20 is the fluorescence observation endoscope 10 by reading the identification data stored in the ROM 17.

Based on a command from the system controller 70, the timing controller 71 controls the laser driver 52 to carry out the intermittent ON/OFF operation of the excitation light at predetermined timing, and further controls the second motor driver 54 that drives the shutter driving motor 38 to carry out the intermittent ON/OFF operation of the white light at predetermined timing. The timing controller 71 also controls the timing when the imaging device 13 takes an image through the CCD driver 56, and further controls the data read/write operation of each of the image memories 58a-58c (the address data controls), indicating the respective timings of the image signal processing for the pre-signal-processing circuit 57 and the post-signal-processing circuit 59. In addition, the pre-signal-processing circuit 57 controls the first motor driver 53 that drives the aperture driving motor 31 to adjust the intensity of the white light and the brightness of the normal image on the monitor 60 according to the brightness level of the image signals inputted during the time to take a normal image. The post-signal-processing circuit 59 controls the timing for the image to be scaled up and down, to be given the aspect ratio conversion, and to be displayed on the basis of a command from the timing controller 71.

Next, the operation of the endoscope system of the embodiment constituted as mentioned above is explained. The endoscope system of the embodiment operates in any one of the following three modes as moving image modes: a normal image display mode in which the normal (color) image taken with the white light applied continuously is displayed as a moving image; a fluorescence image display mode in which the fluorescence image taken with the excitation light applied continuously is displayed as a moving image; and a simultaneous display mode in which the normal image and the fluorescence image taken with the white light and the excitation light alternately applied are displayed as moving images. When a fluorescence mode switch 73 provided at the operation part 10b of the fluorescence observation endoscope 10 is OFF, the system is set up in the normal image display mode. If the fluorescence mode switch is turned ON, the system will be set up in either the fluorescence image display mode or the simultaneous display mode. It can be previously defined with the switches that are provided on the switch panel 23 which mode will be selected. Hereinafter, each mode is explained. In addition, although the still image of the corresponding one of the normal image and the fluorescence image can be observed by pushing the still image switch 73 in each display mode, the detailed explanation about the display of the still image is omitted.

When the fluorescence mode switch 73 is OFF, the system is set up in the normal image display mode, as described above. In the normal observation mode, the system controller 70 controls the third motor driver 55 to drive the unit driving motor 42 and shift the unit 40 to a point out of the white light path, and further controls the lamp driving power supply 51 to let the white light source 30 emit the white light continuously. At this time, the shutter driving motor 38 and the excitation light source are not driven, but still OFF. Thereby, the white light emitted from the white light source 30 is continuously introduced into the light guide 16. The imaging device provided at the tip of the fluorescence observation endoscope captures the image of the inside of the body cavity illuminated with the white light. The normal image signals outputted from the imaging device 13 are inputted into the pre-signal-processing circuit 57 through the cable driver 15 and the signal cable 18.

The pre-signal-processing circuit 57, based on the signals from the timing controller 71, allows the first image memory 58a and the second image memory 58b to store the normal image signals. The post-signal processing circuit 59, based on the signals from the timing controller 71, reads out the image signals from the first image memory 58a and the second image memory 58b, and converts the image signals into the video signals, displaying a single moving normal image in full screen on the monitor 60.

If the fluorescence mode switch 73 is turned ON in the normal image display mode, the system will be set up in either mode between the fluorescence image display mode and the simultaneous display mode, the mode which is previously defined by the switches on the switch panel 23. When the system is set up in the fluorescence image display mode by the switches on the switch panel 23, the system controller 70 controls the third motor driver 55 to drive the unit driving motor 42 so that the unit 40 is shifted to a point on the white light path, and controls the lamp driving power supply 51 to turn OFF the white light source 30, and further controls the laser driver 52 to let the excitation light source 33 emit the excitation light continuously. The shutter driving motor 38 is still OFF. Thereby, the excitation light emitted from the excitation light source 33 is continuously introduced into the light guide 16. The imaging device 13 provided at the tip of fluorescence observation endoscope captures the image of fluorescence emitted from the body cavity excited by the excitation light. The fluorescence image signals outputted from the imaging device 13 are inputted into the pre-signal-processing circuit 57 through the cable driver 15 and the signal cable 18.

Figure 5:
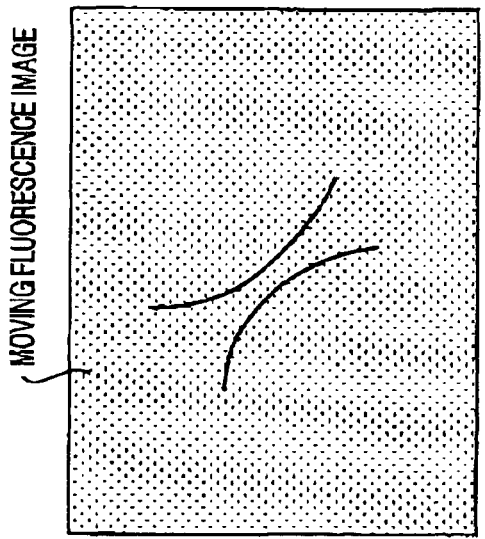
FIG. 5 shows an example of a screen displayed on a monitor in a fluorescence image display mode.

The pre-signal-processing circuit 57 allows the first and second memories 58a, 58b to store the fluorescence signals, based on the signals from the timing controller 71. The post-signal-processing circuit 59, based on the signals from the timing controller 71, reads out the image signals from the first and second memories 58a, 58b to convert the image signals into the video signals, displaying a single fluorescence image as a moving image on the monitor 60. FIG. 5 shows an example of the screen that is displayed on the monitor 60 in the fluorescence image display mode. Since the image data captured by the imaging device 13 has the same aspect ratio of 4:3 as the display area of the monitor 60, the fluorescence image, as well as the normal image, is displayed in a full screen view coinciding with the display area of the monitor 60 without carrying out special conversion processing.

When the fluorescence mode switch 73 is turned ON and the simultaneous display mode is applied by the switches on the switch panel 23, the system controller 70 controls the third motor driver 55 to drive the unit driving motor 42 so that the unit 40 is shifted to the point on the white light path units, and further controls the lamp driving power supply 51 to let the white light source emit continuously. The timing controller 71 controls the second motor driver 54 to rotate the shutter driving motor 38, and further controls the laser driver 52 to turn OFF the excitation light source 33 while the window 37a of the rotary shutter 37 is located on the white light path (while the white light is introduced into the light guide) and generate the excitation light while the shielding part of the rotary shutter 37 is located on the white light path (while the white light is not introduced into the light guide). Thereby, an object is irradiated alternately with the white light and the excitation light. The imaging device 13 provided at the tip of the fluorescence observation endoscope alternately takes the normal image of the body cavity wall illuminated with the white light and the fluorescence image of the body cavity wall excited by the excitation light. The image signals outputted from the imaging device 13 is inputted into the pre-signal-processing circuit 57 through the cable driver 15 and the signal cable 18.

Figure 6:
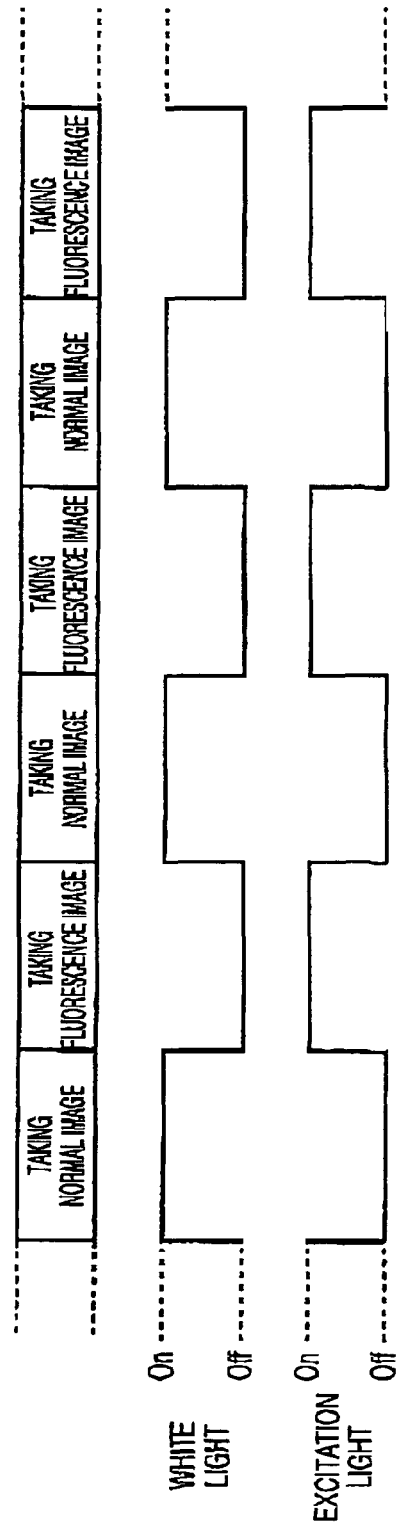
FIG. 6 is a chart illustrating the respective irradiation timings of white light and excitation light and the respective timings when the two kinds of image data are outputted from an imaging device in a simultaneous display mode.

FIG. 6 is a chart pattern showing the respective irradiation timings of the white light and the excitation light in the simultaneous display mode and the timing when image data is outputted from the imaging device. As shown in FIG. 6, the normal color image is taken while the white light is applied and the excitation light is not applied, and the fluorescence image is taken while the white light is not applied and the excitation light is applied.

Based on the signals from the timing controller 71, the pre-signal-processing circuit 57 allows the first image memory 58a to store the normal image signals and the second memories to store the fluorescence image signals. Based on the signals from the timing controller 71, the post-signal-processing circuit 59 reads out the respective image signals from the first and second memories, and performs scan conversion for the respective image signals, which are then displayed as a moving normal image and a moving fluorescence image on the monitor 60, respectively.

Figure 7:
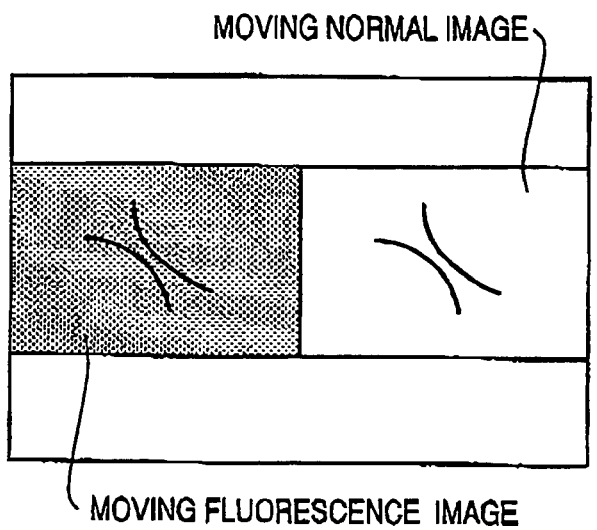
FIG. 7 shows an example of a screen displayed on the monitor when both of two conversion-assignment switches are OFF in the simultaneous display mode.

The display aspect on the monitor 60 in the simultaneous display mode varies depending on the ON/OFF states of first and second conversion-assignment switches 74 and 75. When both of the two switches 74 and 75 are OFF, the normal image and the fluorescence image are displayed side by side with the same aspect ratio (4:3) as each image displayed separately, as shown in FIG. 7. Supposing that the lengths of the long (horizontal) and short (vertical) components of the monitor's display area are x and y, respectively, and the normal image and the fluorescence image have no blank space, each image will be (x/2)×(y/2), and the display magnification in this case will be one-half times higher than when each image is displayed separately. Although the whole of each image can be checked under such a display condition, it might be difficult to check the detail thereof because of low display magnification.

Figure 8:
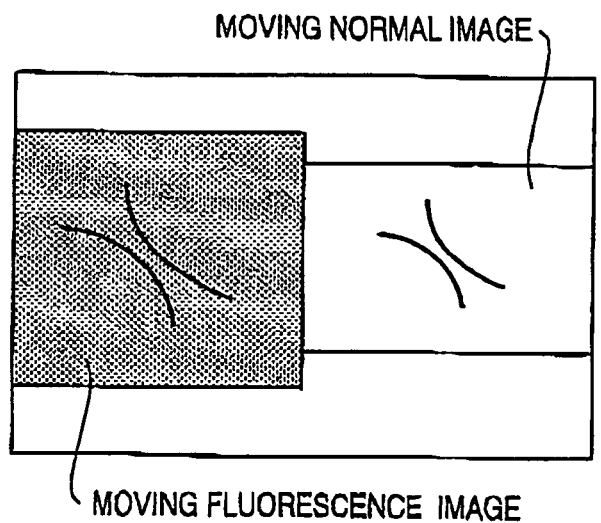
FIG. 8 shows an example of a screen displayed on the monitor when either one of the two conversion-assignment switches is ON in the simultaneous display mode.

Therefore, when it is necessary to make an observation with higher display magnification, at least one of the first and second conversion-assignment switches 74 and 75 is turned ON. If the first conversion-assignment switch 74 is turned ON and the second conversion-assignment switch 75 is turned OFF, the aspect ratio of the fluorescence image will be converted into 1:1, and both lateral ends thereof will be cut so that the center portion thereof can be displayed with higher magnification than the example in FIG. 7. The normal image is displayed in the same way as shown FIG. 7. The fluorescence image in this case is (x/2)×(x/2). Considering the size of the vertical component which are not cut, since x equals (4/3)y, x/2=2y3. Consequently, the display magnification of the fluorescence image in FIG. 8 is about 0.67 times larger than when the fluorescence image is displayed separately. In general, a portion to observe is located in the center of the display area. Accordingly, even if both lateral ends are cut as mentioned above, there is almost no trouble in making a diagnosis, and thus the diagnosis becomes easier since it is possible to make an observation with higher magnification than when the perfect image is displayed.

When the first conversion-assignment switch 74 is turned OFF and the second conversion-assignment switch 75 is turned ON, the aspect ratio of the normal image is converted into 1:1, and both lateral ends thereof are cut so that the center portion thereof is displayed with higher magnification than the example of FIG. 7. The fluorescence image is displayed in the same way as indicated in FIG. 7.

Figure 9:
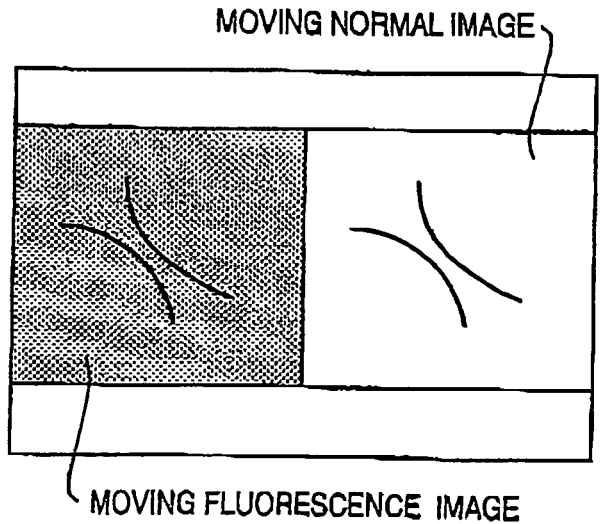
FIG. 9 shows an example of a screen displayed on the monitor when both of the two conversion-assignment switches are ON in the simultaneous display mode.

When both of the first and second conversion-assignment switches 74 and 75 are turned ON, as shown in FIG. 9, both aspect ratios of the fluorescence image and the normal image are converted into 1:1, and both lateral ends of each image are cut so that the center portion thereof is displayed with higher magnification than the example of FIG. 7.

Thus, in the simultaneous display mode, by operating the conversion-assignment switch, either one of the aspect ratios of the fluorescence image and the normal image or both is converted so that the center portion of the corresponding image is displayed with higher magnification than before conversion. Consequently, it becomes easier to make a diagnosis while observing the details of the image and to check a pathological change part.

Figure 10:
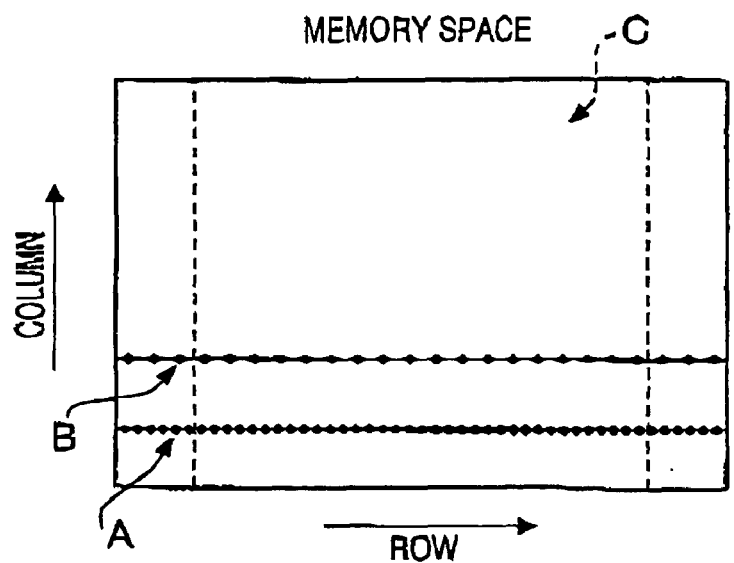
FIG. 10 shows a memory space of an image memory.

Each of the image memories 58a-58c is provided with memory space as shown in FIG. 10, and is specified and controlled by address signal so that the image data is written in thereto or read out therefrom. The memory space has two-dimensional array of memory cells, and the address of a specific memory cell is specified by specifying a row (line in the lateral direction) and a column (line in the vertical direction). In the case of storing the image data, a pixel of value of the image data is stored in one memory cell, and the values of the horizontally-aligned image pixels are allocated to the memory cells aligned in the row direction while the values of the vertically-aligned image pixels are allocated to the memory cells aligned in the column direction.

Supposing the image data based on the image signals obtained by the imaging device 13 is allocated to the entire memory space, when a single image is displayed on the monitor 60 as shown in FIG. 5, the video signals are generated by reading out values which are stored in all memory cells in the entire memory space in sequence. The data for one row is allocated to one scanning line. A row A in FIG. 10 shows an aspect that the data are read out from all memory cells (black dots) in the row. The data are read out from all memory cells in a column as well.

On the other hand, as shown in FIG. 7, when the normal image and the fluorescence image are reduced to be displayed, the video signals are generated by intermittently reading out values stored in the memory cells from the entire memory space. That is, for example, a value is read out from every other memory cell depending on reduction magnification. A row B in FIG. 10 shows an aspect that the data is read out from every other memory cell (black dot) in the row. The data are intermittently read out from memory cells in a column as well.

Furthermore, when the aspect ratios of the normal image and the fluorescence image are converted as shown in FIG. 9, only the image data within an area shown by a reference character C is used without using both lateral sides of the image data outside the boundary indicated by a dashed line in FIG. 10. Additionally, when plurality of images are displayed on the same display area as shown in FIGS. 7-9, the timing controller 71 outputs control signals simultaneously to plurality of image memories to read out and display the data in parallel.

Figure 11:
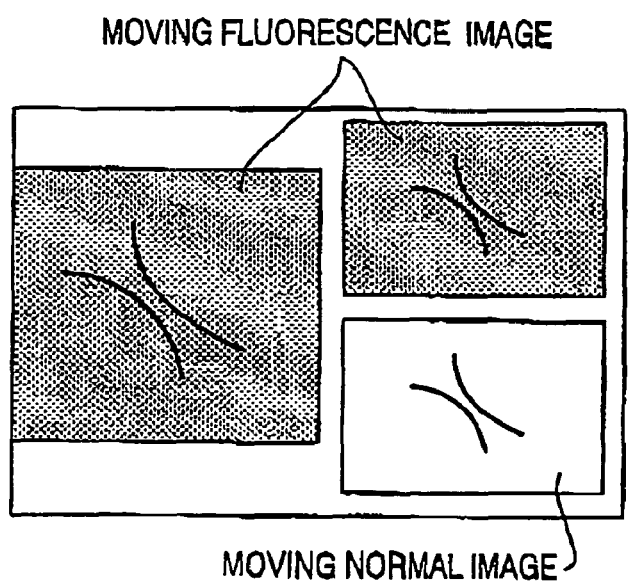
FIG. 11 shows another example of a screen displayed on the monitor in the simultaneous display mode.
Figure 12:
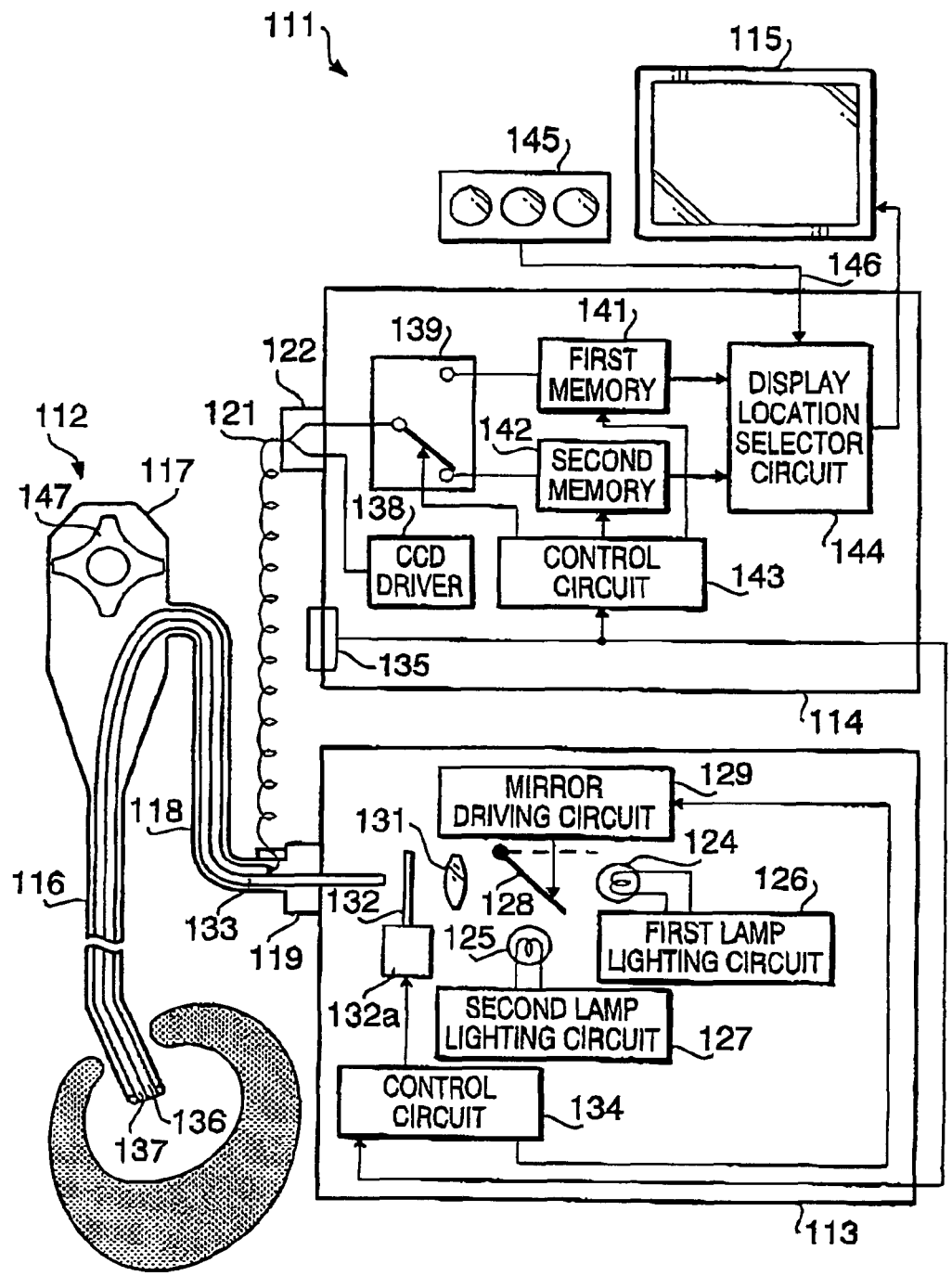
FIG. 12 is a block diagram showing a configuration of a conventional electronic endoscope system.

Although the embodiment is configured to display a total of two images—one normal image and one fluorescence image in the simultaneous display mode in the above explanation, it is further possible to display three or more images simultaneously depending on the setting of the switches on the switch panel 23. For example, as shown in FIG. 11, it is possible to display the fluorescence image that is converted into an image with a 1:1 aspect ratio to be magnified on the left side of the display area, and to display the fluorescence image and the normal image that are reduced without the aspect ratio conversion one above the other on the right side of the display area. In this case, all of the first-third image memories 58a, 58b, and 58c are used.

In addition, although the embodiment is adapted to assign the aspect ratio conversion with the conversion-assignment switches 74 and 75 that are provided at the operation part 10b of the fluorescence observation endoscope 10, it may be allowable to always display converted images as shown in FIG. 9 without providing such switches in the simultaneous display mode.

The present disclosure relates to the subject matter contained in Japanese Patent Application No. P2004-191932, filed on Jun. 29, 2004, which is expressly incorporated herein by reference in its entirely.

What is claimed is:

1. An electronic endoscope system configured to observe living tissues inside a body cavity, comprising:

an image capturing system configured to capture images of the living tissues;

a displayer having an image displaying area, each of the images captured by the image capturing system and the image displaying area having substantially a same rectangular shape defined by a predetermined aspect ratio;

a display control system that controls the displayer to display a plurality of images in the image displaying area of the displayer along a predetermined direction parallel to one side of the rectangular shape;

a data conversion system that converts the predetermined aspect ratio of at least one of the plurality of images displayed in the image displaying area such that at least one of both sides of the at least one image in the predetermined direction is eliminated, a remaining portion of the converted image being displayed in such an enlarged manner that a length of the converted image in the predetermined direction is unchanged on the image displaying area, wherein at least one of the plurality of images is configured to be enlarged independently of the other of the plurality of images while the plurality of images are displayed in the image displaying area;

a first conversion-assignment switch configured to independently enlarge the at least one of the plurality of images; and a second conversion-assignment switch configured to independently enlarge at least one of the other plurality of images, wherein when the first conversion-assignment switch is turned OFF and the second conversion-assignment switch is turned ON, the aspect ratio of the normal image is converted into 1:1, and both lateral ends thereof are cut so that the center portion thereof is displayed with higher magnification.

2. The electronic endoscope system according to claim 1, wherein the display control system controls the displayer to display the plurality of images in the image displaying area along a direction parallel to a longer side of the rectangular shape of the image displaying area.

3. The electronic endoscope system according to claim 2, wherein the data conversion system converts at least one of the plurality of images to be displayed in the image displaying area such that both sides of the image in the predetermined direction are eliminated, the remaining portion of the converted image being displayed such that a length of the converted image in the predetermined direction is unchanged on the image displaying area.

4. The electronic endoscope system according to claim 2, further comprising at least one operator to be operated by a user to specify images to be converted by the data conversion system.

5. The electronic endoscope system according to claim 1, further comprising at least one operator to be operated by a user to specify images to be converted by the data conversion system.

6. The electronic endoscope system according to claim 1, further comprising:

an electronic endoscope that includes an insertion part which is inserted in the body cavity;

a light guide which introduces illuminating light to the tip of the insertion part;

an illuminating apparatus having a white light source emitting white light and an excitation light source that emits excitation light having a predetermined wavelength, the living tissues fluoresce to emit auto fluorescence when irradiated with the excitation light; and an illuminating control system that controls the illuminating apparatus such that the white light source and the excitation light source illuminate the living tissues alternately at every predetermined period, wherein the display control system that controls the displayer to display the plurality of images which includes a normal image generated while the living tissues are illuminated with the white light and a fluorescence image generated while the living tissues are irradiated with the excitation light.

7. The electronic endoscope system according to claim 6, wherein the electronic endoscope includes a ROM that stores an identification data identifying a kind of electronic endoscope connected to the illuminating apparatus.

8. The electronic endoscope system according to claim 6, wherein the illuminating apparatus includes a rotary shutter provided in front of the white light source, the rotary shutter having a light transmitting area and a light blocking area, the white light intermittently illuminating the living tissues as the rotary shutter rotates.

9. The electronic endoscope system according to claim 8, wherein the illuminating apparatus includes an excitation light source driver that intermittently turns ON/OFF the excitation light source synchronously with blocking/transmitting of the white light.

10. The electronic endoscope system according to claim 8, wherein the rotary shutter is able to be shifted together with a beam combiner to a point where the rotary shutter does not interfere with the white light, the beam combiner combining both light paths of the white light and the excitation light.

11. The electronic endoscope system according to claim 1, wherein the data conversion system comprising:

a pre-signal-processor that processes image signals received from the image capturing system;

at least two image memories that temporarily store the image signals outputted from the pre-signal-processor; and a post-signal-processor that performs image-conversion against the image signals outputted from the image memories and further transforms the converted signals into standardized video signals which are allowed to be displayed on the displayer.

12. The electronic endoscope system according to claim 1, wherein the image capturing system comprises:

an objective lens that first receives light from the living tissues and forms an image thereof;

an imager that receives the formed image and outputs an image signal corresponding to the received image; and an excitation light cut filter that is provided between the objective lens and the imager, wherein the excitation light cut filter eliminates the wavelength components equivalent to the excitation light from light directed to the imager from the objective lens.

13. The electronic endoscope system according to claim 12, wherein the excitation light source emits near-ultraviolet light.

14. The electronic endoscope system according to claim 1, wherein the plurality of images comprises first and second images, wherein the predetermined aspect ratio of the first and second images are converted at a ratio of 1:1 by the data conversion system, and both sides of each of the first and second images are eliminated so that center portions of the first and second images are magnified.

15. The electronic endoscope system according to claim 1, wherein the plurality of images are displayed side-by-side in the image displaying area.

16. An electronic endoscope system used configured to observe inside a body cavity, comprising:

an image capturing system configured to capture images of the living tissues;

a displayer having an image displaying area, each of the images captured by the image capturing system and the image displaying area having substantially a same rectangular shape defined by a predetermined aspect ratio;

a display control system that controls the displayer to display a plurality of images in the image displaying area of the displayer along a predetermined direction parallel to one side of the rectangular shape;

a data conversion system that converts the predetermined aspect ratio of at least one of the plurality of images displayed in the image displaying area such that at least one of both sides of the at least one image in the predetermined direction is eliminated so that the aspect ratio of the at least one of the plurality of images displayed on the image displaying area is changed, the converted image being displayed such that a length of the converted image in the predetermined direction is unchanged on the image displaying area, wherein at least one of the plurality of images is configured to be enlarged independently of the other of the plurality of images while the plurality of images are displayed in the image displaying area;

a first conversion-assignment switch configured to independently enlarge the at least one of the plurality of images; and a second conversion-assignment switch configured to independently enlarge at least one of the other plurality of images, wherein when the first conversion-assignment switch is turned OFF and the second conversion-assignment switch is turned ON, the aspect ratio of the normal image is converted into 1:1, and both lateral ends thereof are cut so that the center portion thereof is displayed with higher magnification.

17. An electronic endoscope system configured to observe living tissues inside a body cavity, comprising:

an image capturing system configured to capture images of the living tissues;

a displayer having an image displaying area, each of the images captured by the image capturing system and the image displaying area having substantially a same rectangular shape defined by a predetermined aspect ratio;

a display control system that controls the displayer to display a plurality of images in the image displaying area of the displayer along a predetermined direction parallel to one side of the rectangular shape;

a data conversion system that converts the predetermined aspect ratio of at least one of the plurality of images displayed in the image displaying area such that at least one of both sides of the at least one image in the predetermined direction is eliminated, a remaining portion of the converted image being displayed in such an enlarged manner that a length of the converted image in the predetermined direction is unchanged on the image displaying area, wherein at least one of the plurality of images is configured to be enlarged independently of the other of the plurality of images while the plurality of images are displayed in the image displaying area;

a first conversion-assignment switch configured to independently enlarge the at least one of the plurality of images; and a second conversion-assignment switch configured to independently enlarge at least one of the other plurality of images, wherein when both of the first and second conversion-assignment switches are turned ON, both aspect ratios of the fluorescence image and the normal image are converted into 1:1, and both lateral ends of each image are cut so that the center portion thereof is displayed with higher magnification.

18. An electronic endoscope system used configured to observe inside a body cavity, comprising:

an image capturing system configured to capture images of the living tissues;

a displayer having an image displaying area, each of the images captured by the image capturing system and the image displaying area having substantially a same rectangular shape defined by a predetermined aspect ratio;

a display control system that controls the displayer to display a plurality of images in the image displaying area of the displayer along a predetermined direction parallel to one side of the rectangular shape;

a data conversion system that converts the predetermined aspect ratio of at least one of the plurality of images displayed in the image displaying area such that at least one of both sides of the at least one image in the predetermined direction is eliminated so that the aspect ratio of the at least one of the plurality of images displayed on the image displaying area is changed, the converted image being displayed such that a length of the converted image in the predetermined direction is unchanged on the image displaying area, wherein at least one of the plurality of images is configured to be enlarged independently of the other of the plurality of images while the plurality of images are displayed in the image displaying area;

a first conversion-assignment switch configured to independently enlarge the at least one of the plurality of images; and a second conversion-assignment switch configured to independently enlarge at least one of the other plurality of images, wherein when both of the first and second conversion-assignment switches are turned ON, both aspect ratios of the fluorescence image and the normal image are converted into 1:1, and both lateral ends of each image are cut so that the center portion thereof is displayed with higher magnification.

* * * * *